United States Patent [19]

Schumann, Jr. et al.

[11] 4,029,419

[45] June 14, 1977

[54] TEXTILE COLOR ANALYZER CALIBRATION

[75] Inventors: Paul A. Schumann, Jr., Wappingers Falls; Alvin H. Tong, Poughkeepsie, both of N.Y.

[73] Assignee: International Business Machines Corporation, Armonk, N.Y.

[22] Filed: Oct. 10, 1975

[21] Appl. No.: 621,334

[52] U.S. Cl. .............................. 356/173; 250/226; 356/188; 356/189; 356/210; 356/212; 356/243
[51] Int. Cl.[2] ..................... G01J 3/50; G01N 21/48
[58] Field of Search ... 356/173, 179, 186, 188–190, 356/195, 209–212, 236, 243; 250/226, 228

[56] References Cited

UNITED STATES PATENTS 2,774,276 12/1956 Glasser et al. ..................... 356/176
3,874,799 4/1975 Issacs et al. ........................ 356/173

*Primary Examiner*—F. L. Evans
*Attorney, Agent, or Firm*—Douglas R. McKechnie

[57] ABSTRACT

A spectrophotometer is operative to measure or analyze the colors of materials such as textiles. A test sample is held by a holder and is illuminated by polychromatic light. Diffuse light reflected from the sample is collected and converted to variable monochromatic light and detected. The system is calibrated by using a secondary white standard calibrated against a primary white standard, by using a black standard to compensate for dark current and internal reflectance from a pressure plate, and by using a mirror to obtain internal wall reflectance used in a correction factor.

7 Claims, 4 Drawing Figures

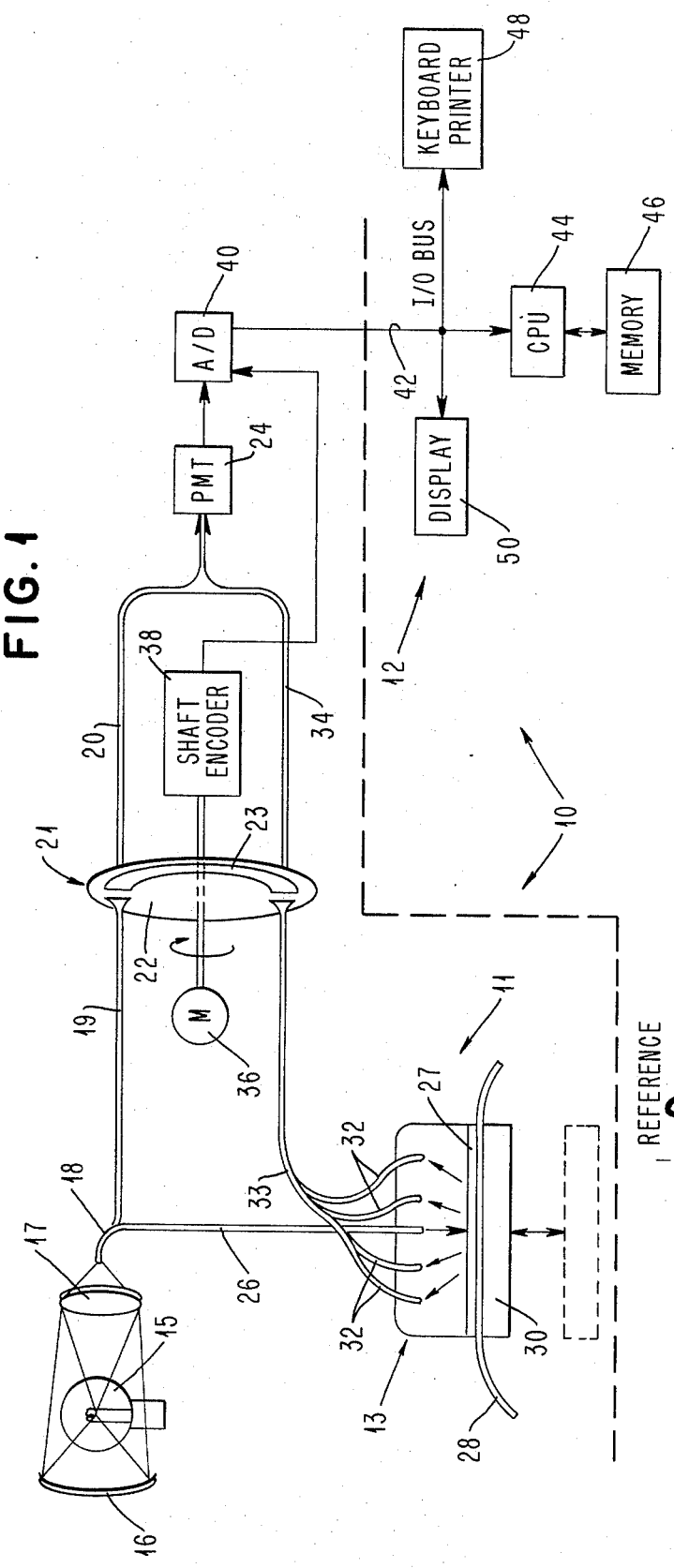
FIG. 1
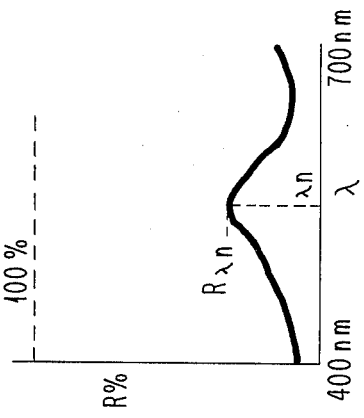
FIG. 4
FIG. 3
FIG. 2

TEXTILE COLOR ANALYZER CALIBRATION

RELATED PATENT APPLICATIONS

Filed concurrently herewith are the following applications each of which is assigned to the assignee of the present application:

Application A — "Apparatus for Textile Color Analysis," by H. M. Demsky et al., Ser. No. 621,333, filed Oct. 10, 1975.

Application B — "Apparatus for Textile Color Analysis", by H. M. Demsky et al., Ser. No. 621,335, filed Oct. 10, 1975.

Applications A and B are directed to different inventive aspect of apparatus embodied in the spectrophotometer involved in the present invention.

FIELD OF THE INVENTION

This invention relates to spectrophotometry and, more particularly, to the calibration of a spectrophotometer system particularly adapted for analyzing the colors of materials such as textiles and including apparatus disclosed and claimed in the above applications.

PRIOR ART

In spectrophotometry, it has been customary to use white and black standards to establish 100% and 0% reflectance values. After being thus calibrated, reflectance of a test sample is measured and determined or calculated relative to such values.

Also known in the prior art are spectrophotometers that include or are connectable to a computer to provide a high speed system for automatically measuring the sample, storing calibration factors, and calculating the reflectance of the sample. An example of such a system is disclosed in U.S. Pat. No. 3,751,643 which discloses a spectrophotometer primarily intended for measuring the thickness of thin film on silicon substrate by measuring reflectance. The present invention includes a similar system.

SUMMARY OF THE INVENTION

One of the objects of the invention is to provide a spectrophotometer for analyzing colors that is fast, automatic and accurate.

Another object is to provide a spectrophotometer having apparatus of the type disclosed in the above related applications, with means to calibrate the system to provide measurement results that are highly accurate and reproducible.

A further object is to provide a novel method for calibrating an instrument for measuring or analyzing the color of a textile sample.

Still another object is to calibrate a color analyzer to compensate for internal reflections in an instrument head.

Another object is to calibrate a spectrophotometer initially on a primary standard and to thereafter calibrate the apparatus using a secondary standard.

A still further object is to provide a textile color analyzer having a measuring head using a glass plate for compressing a textile sample, wherein calibration measurements are made to compensate for the reflectance of the glass plate.

Another object is to provide a spectrophotometer which calculates the reflectance of a test sample allowing compensation to be made for specular reflections from the sample and from a standard.

Briefly, the invention comprises spectrophotometer having a measuring head adapted to press a test sample between a glass plate and back-up pad. The sample is illuminated and diffuse reflections are collected, the light being of variable wavelength across the range of wavelengths of visible light. Calibration measurements are made on a black standard to compensate for dark current and reflectance of the glass plate, on a primary white standard to determine 100% value, on a secondary white plaque to determine a scaling factor relative to the 100% line, and on a test sample the color of which is to be analyzed. A mirror is used to determine the internal wall reflectance. The reflectance of the test sample is calculated using the above factors.

Other objects and advantages of the invention will be apparent from the following detailed description of a preferred embodiment of the invention taken in connection with the accompanying drawing wherein:

FIG. 1 is a schematic diagram of a spectrophotometer embodying the invention;

FIG. 2 is an illustrative graph showing the output of the detector shown in FIG. 1, for one revolution of the monochromator wheel while making a measurement;

FIG. 3 is an illustrative graph showing the various signal ratios obtained during operation of the spectrophotometer; and FIG. 4 is an illustrative graph of the reflectance of a test sample at different wavelengths.

DETAILED DESCRIPTION

Referring now to the drawing, and first to FIG. 1, the preferred embodiment of the invention there shown comprises a spectrophotometer 10 including a transducing or instrument section 11 and a computer or data processing section 12. The instrument section comprises a head 13 constructed in accordance with the description in the above related dockets, incorporated herein by reference. The remaining portions are similar to those disclosed in the above mentioned patent.

A polychromatic light source 15 emits light towards a reflector 16 and lens 17. The reflector directs the light received thereby towards the lens and the lens concentrates the light received directly from source 15 and from reflector 16 into the entrance of a fiber optic bundle or light pipe 18.

The exit end of light pipe 18 is bifurcated to form part of a reference path and a sample path, the reference path including a light pipe 19 whose exit end is fanned out into a narrow rectangular face aligned with a similar face of a fiber optic bundle 20 disposed on the other side of a monochromator wheel 21. Wheel 21 includes an opaque portion 22 and a wedge type variable interference filter 23 that is ring shaped and extends for 180° around and concentric to the axis of wheel 21. As wheel 21 is rotated, light from bundle 19 will be transmitted to bundle 20 during one half of the revolution when filter 23 is located therebetween. During the other half, opaque portion 22 blocks the transmission of light. The exit end of bundle 20 is connected to a detector such as a photo multiplier tube (PMT) 24.

The sample path includes a light pipe 26 having an exit end that terminates in head 13 and functions to transmit light therealong so as to illuminate a test sample 28 pressed between a glass plate 27 and a polyethylene backup pad 30. This pad is movable between the dotted position and full position so as to allow the textile sample 28 to be inserted and removed so that other samples or standards may be placed therebetween.

Light reflected from the sample is collected by four ends 32 of a fiber optic bundle 33 that transmits such light therealong. The end of bundle 33 is fanned out similar to the manner described above with reference to the end of bundle 19 and is in alignment with a similarly shaped end of a bundle 34 disposed on the other side of wheel 21 and connected to PMT 24. The ends of bundles 33 and 34 are diametrically opposite to the ends of bundles 19 and 20 so that light is alternately transmitted along the reference path and the sample path. It is to be appreciated that FIG. 1 is merely a schematic diagram and that the details of the head may be had by reference to the above applications.

Filter wheel or monochromator wheel 21 is rotated by a motor 36 in a predetermined direction and a conventional shaft encoder 38 is connected to rotate with the motor and provide output signals at fixed angular displacements of the wheel. Filter 23 is uniformly graduated from one end to the other to transmit a narrow band of monochromatic light throughout the range of visible light and because of the uniform gradation, the light being transmitted at any position of wheel 21 is a function of the angular displacement which can be obtained by signals from the shaft encoder. PMT 24 provides an output signal proportional to the intensity of light received thereby, and an illustrative diagram of the output signal thereof is shown in FIG. 2 for one revolution of monochromator wheel 21. In FIG. 2, it is assumed that the zero degree position occurs at the blue end of filter 23 and that that light is first transmitted along the sample path or test path. As wheel 21 rotates through the first 180° of revolution, the output of PMT 24 relative to the angular displacement may vary as shown in the drawing. During the second 180° of revolution, light is transmitted along the reference path and the output of PMT 24 is proportional to the intensity of the light received thereby. This system is initially set up so that an equal amount of light passes along both the sample and reference paths. The ratio of the signal $St$ at a given wavelength $\lambda n$ to the reference signal $Sr$ corresponding to wavelength $\lambda n$ provides a signal ratio that is a measure of the reflectance of the sample. That is, it is approximately the ratio of the light reflected by the sample to the incident light received by the sample.

It should be obvious that the output of PMT 24 is an analog signal that can be used in an analog system to drive a plotter or recorder to provide graphs from which measurements could be taken manually and the final reflectance calculations done manually. However, in the preferred embodiment, of the invention, PMT 24 is connected to a conventional analog-to-digital converter (A/D) 40 which in conjunction with signals from shaft encoder 38 provide a series of discrete digital values corresponding to different angular positions or wavelengths. Converter 40 may be connected to the I/O bus 42 of a computing system including a CPU 44 and a memory 46 where the data is transferred under the control of CPU 44 and stored in memory 46. A keyboard printer 48 is preferably connected to the system and acts as a terminal allowing an operator to control operation of the system and obtain a printed output, and a display 50 may be connected to the system to allow an operator to view a display of the results of a measurement. Quite obviously, such a system runs under the control of programs stored in memory 46 and the programs may be conventional or standard in nature. Relative to the computer, the instrument section appears as another I/O device.

In the operation of the system, the output of the PMT as shown in FIG. 2 would be converted into a series of discrete digital values each of which would be associated with a different nominal wavelength. The computer would then compute the signal ratios of $St/Sr$ and a plot of such ratios could be then calculated or made where a typical one would look such as is shown for line T (test) in FIG. 3. The number of discrete points to be calculated is somewhat a function of the signals provided by the shaft encoder and the resolution desired. Commercially available shaft encoders provide signals every 1° of rotation so that 180 separate discrete points could be obtained. However, we found that 16 such discrete points are sufficient to provide readings every 20 nanometers over the range of 400 to 700 nanometers. Thus, the graphs shown represent making determinations at such discrete points and then drawing a curve through the points.

In accordance with the calibration technique of the invention, five different measurements are made for a primary standard, a secondary standard, a black standard, a mirror and a test sample and, during each of the measurements, the signal ratios P, S, B, M, and T respectively are determined. FIG. 3 shows an illustrative chart in which these various signal ratios have been plotted it being recalled that the signal ratio at any given wavelength $\lambda n$ is a ratio $St/Sr$ for the item being measured. When such measurements are made and the signals stored in the memory, calculations can be performed to determine the true or corrected reflectance R of the test sample, an illustrative graph of a typical example being shown in FIG. 4. The significance of these measurements and the calculations will now be discussed.

The primary standard signal ratio P for establishing the 100% reflectance line is obtained by measuring a standard having a coating of barium sulfate. As is known, it is necessary to prepare such standards using barium sulfate powder and that once prepared, such standards are subject to deterioration so that it becomes necessary to prepare new ones from time to time. To avoid such preparation, a secondary standard is used which is a white ceramic plaque that does not deteriorate with time and usage. Thus, the primary standard signal ratio P is determined one time only, the secondary standard signal ratio S is determined at the same time to provide a scaling factor that compensates for any later variations in the system, and the secondary standard can be used at later time to periodically calibrate the system.

A black ceramic plaque is measured to provide a black signal ratio B that represents the zero percent (0%) reflectance line. Such measurement compensates for the dark current of the detector, PMT 24, and for the reflectance of plate 27 which is coated with an anti-reflective coating but nevertheless exhibits a low level of reflectance.

A surface coated mirror is measured to provide a signal ratio M that provides a measure of the internal wall reflectance of head 13.

When such signal ratios have been determined, the calculations below can be made. The calculations are made at each of the discrete wavelengths, eg, every 20 nanometers. The following symbols are used:

P = primary standard signal ratio at a given wavelength $\lambda n$

S = secondary standard signal ratio at a given wavelength $\lambda n$

M = mirror standard signal ratio at a given wavelength $\lambda n$

B = black standard signal ratio at a given wavelength $\lambda n$

T = test sample standard signal ratio at a given wavelength $\lambda n$

Rs = uncorrected reflectance of secondary standard

Rp = reflectance of primary standard

Rt = uncorrected reflectance of test sample $$Rt = \frac{T-B}{S-B} \times \frac{Rs}{Rp} \quad (1)$$

$$Rs = \frac{S-B}{P-B} \quad (2)$$

By definition, $Rp = 1$ so that by making the measurements above, the uncorrected reflectance Rt of the test sample can be calculated. This uncorrected value compensates for the dark current and plate reflectance and determines the reflectance of the test sample between the 0 and 100% lines of the black and white standards. The ratio Rs/Rp (Equation 1) is the scaling factor which, with $Rp=1$, reduces to Rs representing the scaling factor.

It can be shown that the corrected or true reflectance $R\lambda n$ of a test sample is given by the formula:

$$R\lambda n = \left\{ \left[ \frac{1 - \gamma As\, Rp + (\gamma - Aw)\, Rw}{2(1 - \gamma As\, Rp - Aw\, Rw)} \right] Rt + \left[ \frac{1 + (\beta - Aw)\, Rw}{2\, As\, \beta} \right] \right\} \times$$

$$\left\{ 1 - \left[ 1 - \frac{4\beta\, As\, Rt\, (1 - Aw\, Rw) \left[ \frac{1 - \gamma As\, Rp - Aw\, Rw}{1 - \gamma As\, Rp + (\gamma - Aw)\, Rw} \right]}{\left[ \beta\, As\, Rt + \left( \frac{1 - \gamma As\, Rp - Aw\, Rw}{1 - \gamma As\, Rp + (\gamma - Aw)\, Rw} \right) \left( 1 + (\beta - Aw)Rw \right) \right]^2} \right]^{1/2} \right\}$$

$Rw$ = reflectance of wall (3)

$$Rw = \frac{1 - As}{\frac{1}{RMT} + Aw - 1} \quad (4)$$

where
- $As$ = fractional area of sample
- $Aw$ = fractional area of internal wall of head and $As + Aw = 1$ The fractional areas are dependent on the geometry of the instrument and have to be determined beforehand and the values stored. RMT — uncorrected reflectance of mirror $$RMT = \frac{M-B}{S-B} \times \frac{Rs}{Rp} \quad (5)$$

Equations (4) and (5) define terms in (3) and the only terms undefined so far are $\beta$ and $\gamma$.

$\beta$ is the specular multiplier for a test sample. If the specular component of reflections from a sample is known, the $\beta$ factor allows it to be compresentated for. For a specular component, eg, of .2, $\beta = 1.2$. IF $\beta$ is not known, assume the specular component is low or negligible and $\beta = 1$ and thus may be dropped from equation (3). This assumption is valid because the instrument head is designed to minimize the specular component, as described in said Applications.

$\gamma$ is the specular multiplier for the primary standard and allows the specular reflectance of such standard to be compensated for. $\gamma$ is assumed to be 1 for the same reasons as $\beta$.

In summary, the corrected reflectance $R\lambda n$ represents the true reflectance of the test sample and it includes factors that account for the internal wall reflectance, the head geometry, and the specular multipliers for the sample and standard. These multipliers may be neglected as pointed out above in which case equation (3) can be reduced or simplified.

It should be obvious that various changes can be made in the details and arrangements of parts and steps without departing from the spirit and scope of the invention as defined in the appended claims.

What is claimed is:

1. The method of calibrating a spectrophotometer for measuring the reflectance of a test sample, said spectrophotometer comprising an instrument section including a light source, a detector, an opaque head having blackened inner walls defining a chamber and an opening adapted to be positioned next to a test object, first fiber optic means terminating in said chamber for directing light from said light source outwardly through said opening to illuminate a test object thereat, second fiber optic means terminating in said chamber for collecting light reflected from a test object through said opening and conducting such reflected light to said detector whereby said detector provides an output signal proportional to the intensity of light reflected from said test object, the steps comprising:

a. placing a mirror next to said opening as a test object and measuring the amount of light reflected from said inner wall;
   b. placing a white standard next to said opening as a test object and measuring the amount of light reflected therefrom;
   c. calculating the reflectance of said inner wall using the amounts of light measured in steps (a) and (b);
   d. placing a test sample next to said opening as a test object and measuring the amount of light reflected therefrom;
   e. and calculating the true reflectance of said test sample using the amounts of light measured in steps (b) and (d) and said reflectance of said inner wall.

2. The method of claim 1 further comprising the steps of:
   f. placing a black standard next to said opening and measuring the output of said detector,
   and steps (a) and (d) each further comprise subtracting the output of said detector obtained in step (f) from the detector outputs during steps (a) and (d) to determine the amounts of light measured therein.

3. The method of claim 1 wherein said white standard is a secondary standard calibrated against a primary white standard to provide results representing values of 100% reflectance.

4. The method of claim 1 wherein:
   the true reflectance calculated is $R\lambda n$.

5. In a spectrophotometer for measuring the color of a sample, said spectrophotometer having an instrument head for illuminating a test object, and means for collecting diffuse light reflected from said test object and providing an output signal proportional thereto, the combination comprising:
   first means for measuring light reflected from a white primary standard test object and storing a value P indicative thereof;
   second means for measuring a black standard test object and providing and storing a value B indicative of the light reflected therefrom;
   third means for measuring a white secondary standard test object and storing a value S indicative thereof;
   fourth means for calculating the reflectance Rs of said secondary standard and storing the result thereof according to
   $$Rs = \frac{S - B}{P - B};$$
   fifth means for measuring a sample test object and storing a value T indicative thereof;
   sixth means for calculating the reflectance Rt of said sample according to
   $$Rt = \frac{T - B}{S - B} \times Rs;$$
   seventh means operative to illuminate a mirror and detect light reflected from inner walls of said head,
   eighth means for calculating the reflectance of said inner walls,
   and ninth means for calculating the true reflectance of said sample using the factor of said reflectance of said inner walls.

6. The combination of claim 5 comprising tenth means for storing values representing the relative areas of said sample and of said inner walls;
   said ninth means being operative to use said relative areas to calculate said true reflectance.

7. The combination of claim 6 wherein said ninth means is operative to calculate the true reflectance as $R\lambda n$.

* * * * *